United States Patent [19]
Mills

[11] Patent Number: 5,471,999
[45] Date of Patent: Dec. 5, 1995

[54] REUSABLE DUAL FENESTRATION SURGICAL DRAPE

[75] Inventor: Veronica A. Mills, Cincinnati, Ohio

[73] Assignee: Standard Textile Company, Cincinnati, Ohio

[21] Appl. No.: 418,605

[22] Filed: Apr. 7, 1995

[51] Int. Cl.[6] .................................................. A61B 19/00
[52] U.S. Cl. .......................................... 128/849; 128/853
[58] Field of Search ..................................... 128/849–856

[56] References Cited

U.S. PATENT DOCUMENTS

| | | |
|---|---|---|
| 3,797,484 | 3/1974 | Ericson . |
| 3,800,790 | 4/1974 | Collins . |
| 3,942,523 | 3/1976 | Rudtke ..................................... 128/853 |
| 4,196,723 | 4/1980 | Moose, Jr. . |
| 4,414,968 | 11/1983 | Amin . |
| 4,489,720 | 12/1984 | Morris ..................................... 128/853 |
| 5,002,070 | 3/1991 | Taylor ..................................... 128/853 |
| 5,127,423 | 7/1992 | Draeger ................................... 128/849 |
| 5,143,091 | 9/1992 | Patnode ................................... 128/853 |

*Primary Examiner*—Michael A. Brown
*Attorney, Agent, or Firm*—Frost & Jacobs

[57] ABSTRACT

A surgical drape having first and second fenestration portions. A flap member affixed to the drape. The flap member having a portion unattached to the drape and provided with a fenestration of the same size and shape as the first fenestration portion of the drape. The unattached flap portion is shiftable between an unfolded covering position and folded uncovering position. In the unfolded covering position the unattached flap portion overlies the first and second drape fenestration portions with the second fenestration portion being covered thereby and with the flap member fenestration overlying and being co-extensive with the drape first fenestration portion. When the unattached flap member portion is in its folded, uncovering position, both of the first and second drape fenestration portions are exposed.

11 Claims, 4 Drawing Sheets

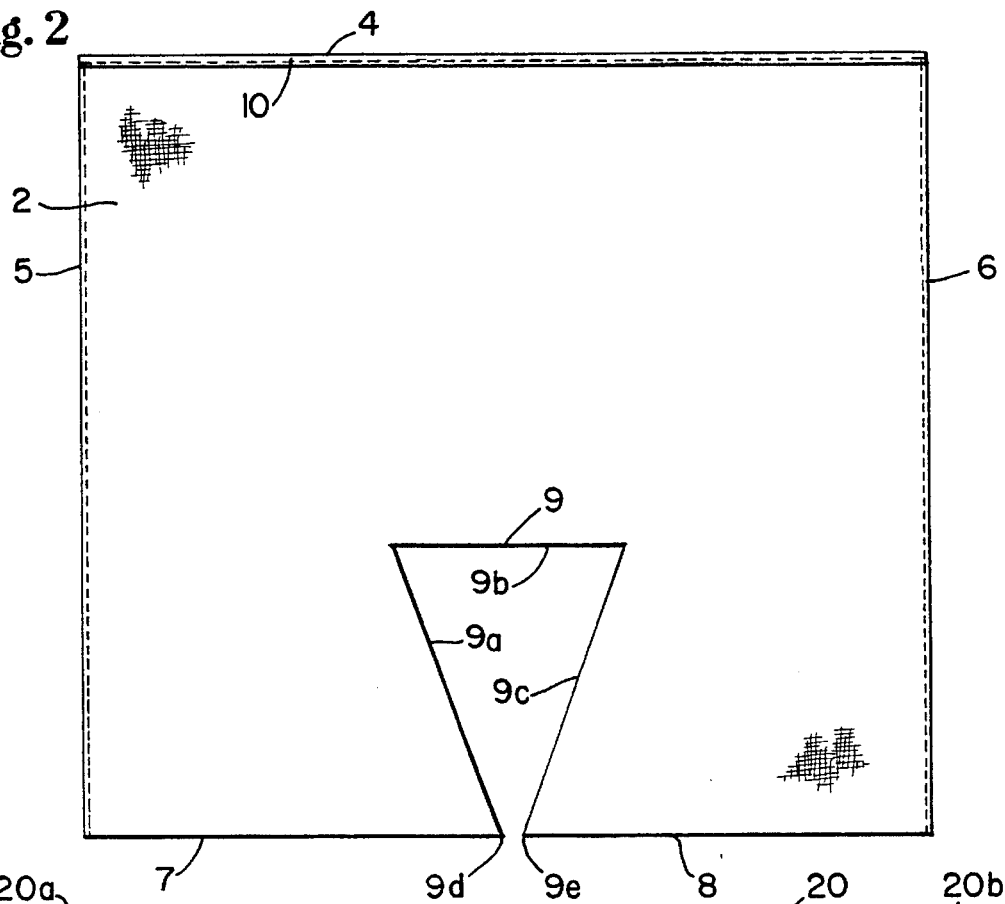
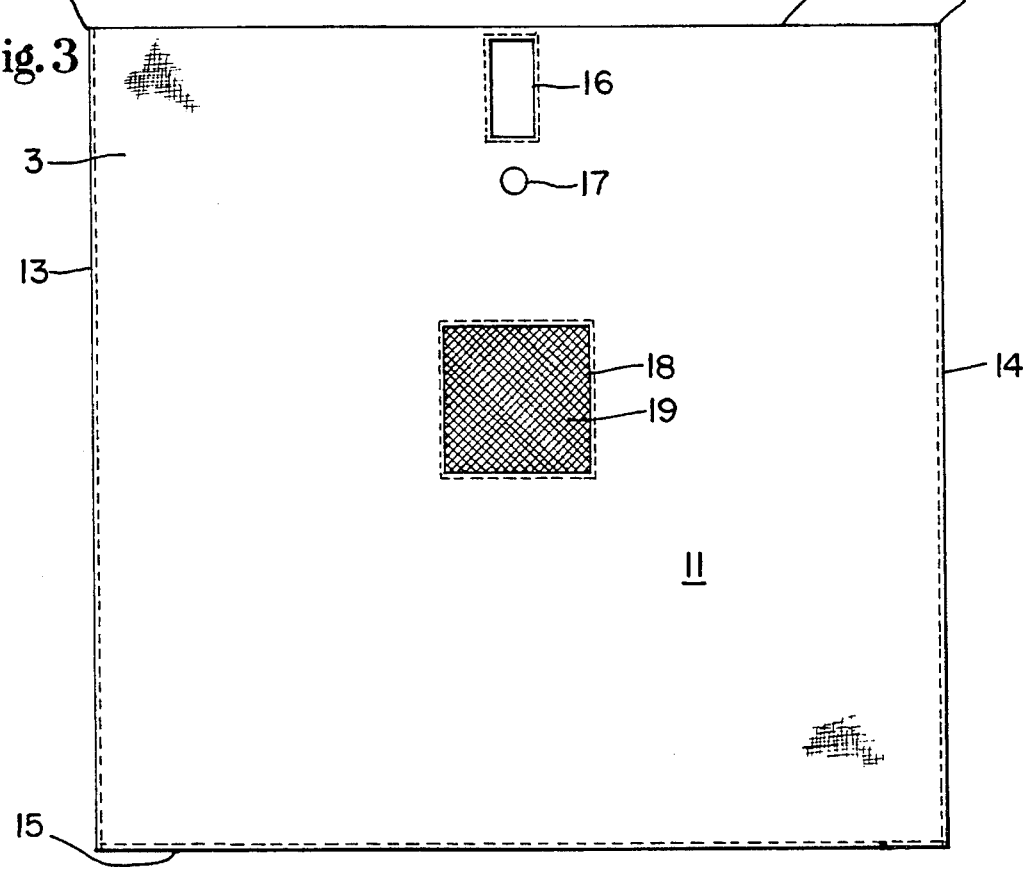

5,471,999

REUSABLE DUAL FENESTRATION SURGICAL DRAPE

TECHNICAL FIELD

The invention relates to a reusable surgical drape having first and second fenestration portions and a flap affixed to the surgical drape at a position near that side of the first fenestration portion opposite the second fenestration portion and being swingable between an unfolded position wherein it covers the second fenestration portion and exposes the first fenestration portion through a flap fenestration of substantially the same size and shape as the first drape fenestration portion, and a folded position in which both drape fenestration portions are exposed.

BACKGROUND ART

The teachings of the present invention are applicable to any drape having two fenestration portions in close proximity, wherein, during a part of the procedure, it is important to have the second fenestration portion covered. An example of such a procedure is a cystoscopic procedure normally followed by a rectal examination. The fenestration portions may constitute parts of a single fenestration, or they may constitute two separate fenestrations in relatively close proximity to each other.

In instances of the type to which the present invention is directed, it is not uncommon to use a disposal drape, provided with a single fenestration. When, during the procedure, a second fenestration portion is needed, the surgeon usually enlarges the original fenestration, or cuts a separate second fenestration.

Prior art workers have devised surgical drapes with dual fenestrations wherein one or the other of the fenestrations may be covered by a single flap located between the fenestrations. While, for many purposes, this type of drape serves well, under some circumstances it has certain drawbacks. For example, the flap, in either of its positions, is always in part at least within the critical zone of the drape (i.e. the zone immediately surrounding the fenestrations or fenestration portions). Furthermore, it precludes the use of a single fenestration with first and second fenestration portions.

The present invention is directed to a reusable drape for any situation wherein one of two fenestrations (or fenestration portions) is preferably covered during a part of the procedure. This can be accomplished by a single flap which is attached to the surgical drape outside the critical zone. The flap has a fenestration formed therein which is of the same size and shape as the first fenestration or fenestration portion formed in the drape. The flap is shiftable between and unfolded position and a folded position. In its folded position, the flap is retracted and lies outside the critical zone of the drape. In its unfolded position, the flap overlies the fenestrations or fenestration portions in the drape, covering the second fenestration or fenestration portion, and with the flap fenestration overlying and being substantially co-extensive with the first fenestration or fenestration portion of the drape.

The surgical drape is preferably made of a top sheet and a bottom sheet so sewn together that gussets are formed to accommodate the legs of the patient. The top sheet is preferably made of a sterilizable low fluid repellant fabric and the bottom sheet is preferably made of two plies of a sterilizable highly fluid repellant fabric. The flap member may be made of a sterilizable, highly fluid repellant fabric inner ply and a sterilizable fluid absorbent and textured fabric outer ply. This enables the first drape fenestration and the flap fenestration to be, when used, surrounded by the fluid absorbent and textured fabric. When the second fenestration or fenestration portion is used, it will be surrounded by the highly fluid repellant fabric.

DISCLOSURE OF THE INVENTION

The invention relates to a surgical drape having first and second fenestration portions which may constitute portions of a single fenestration, or two wholly separate fenestrations in relatively close proximity to each other. A flap member is affixed to the drape and has a fenestration formed therein having the same size and shape as the first fenestration portion.

The flap member has a portion which is not attached to the drape and which is shiftable about a fold line between and unfolded covering position and a folded uncovering position. In the unfolded covering position, the flap member overlies the first and second drape fenestration portions with the drape second fenestration portion being covered thereby and the flap member fenestration overlying the drape first fenestration portion and being substantially co-extensive therewith. When the flap member shiftable portion is in its folded uncovering position, the flap member is out of the critical zone of the drape and both the first and second drape fenestration portions are exposed. Various parts of the drape are made of various types of fabric. The drape may be provided with an opening between the second fenestration portion and the bottom edge of the drape serving as a fluid drainage opening and provided with a fabric net-type filter to collect particulate matter from the fluid flow.

The entire drape is reusable and is sterilizable by any appropriate and well known sterilization method, including autoclaving.

BRIEF DESCRIPTION OF THE DRAWINGS

FIG. 2 is a plan view of the top sheet of the drape of the present invention.

FIG. 3 is a plan view of the bottom sheet of the drape of the present invention.

DETAILED DESCRIPTION OF THE INVENTION

Figure 1:
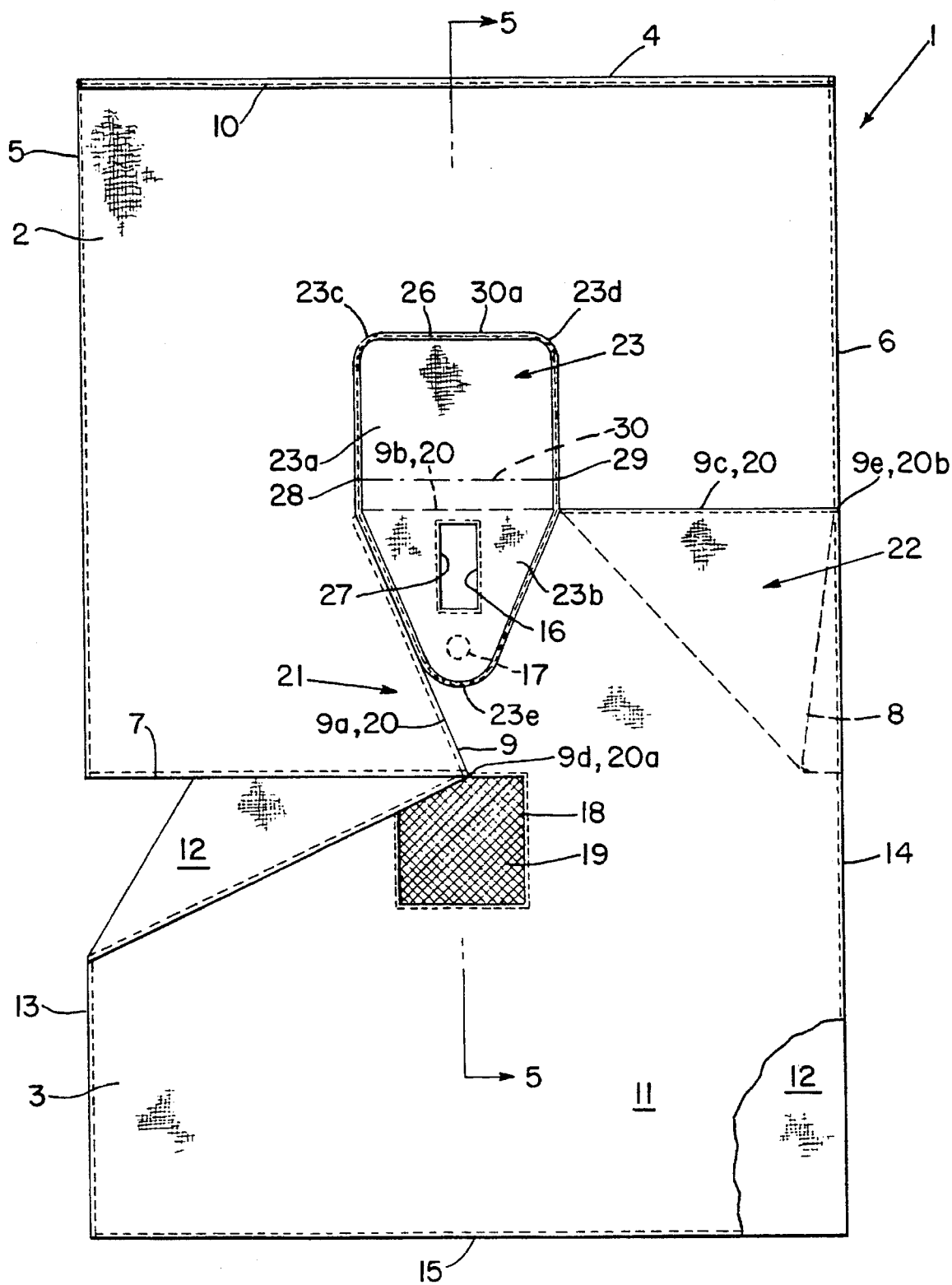
FIG. 1 is a plan view of the drape of the present invention.

In all of the Figures, like parts have been given like index numerals. Reference is first made to FIG. 1 wherein the overall drape is generally indicated at 1. The drape is made up of a top sheet 2 and a bottom sheet 3.

Reference is made to FIG. 2 wherein the top sheet 2 is illustrated. The top sheet comprises a basically rectangular structure having an upper edge 4, side edges 5 and 6 and bottom edge segments 7 and 8. Top sheet 2 has a triangular opening 9 formed therein. The triangular opening 9 has three rectilinear edges 9a, 9b and 9c. The rectilinear edge 9a connects with bottom edge segment 7 as at 9d and the rectilinear edge 9c connects with bottom edge segment 8 as at 9e. The top sheet sides 5 and 6 are hemmed. The top edge 4 may be finished with a brightly colored binding tape 10 to facilitate folding, unfolding and placement of the drape 1. It will be understood that the top edge 4 of top sheet 2 constitutes the top edge of the overall drape 1. Top sheet 2 is preferably made of a single ply of a low liquid repellent fabric such as the material sold by Standard Textile Co., Inc. of Cincinnati, Ohio under the mark WRAPPEL™.

The bottom sheet 3 of the drape 1 comprises a rectangular sheet made up of two fabric plies 11 and 12 (see also FIG. 1). The side edges 13 and 14 and the bottom edge 15 of bottom sheet 3 may be finished in any appropriate manner as, for example, with concealed hems. The bottom edge 15 comprises the bottom edge at the overall drape 1.

The bottom sheet 3 is provided with two fenestrations 16 and 17 and an opening 18. Fenestration 16 provides appropriate access to the patient for cystoscopic procedures. Fenestration 17 provides appropriate access to the patient for a subsequent rectal examination following the cystoscope procedure. The opening 18, the fluid drainage opening, is provided with a co-existence fabric mesh 19. The opening 18 is preferably finished with a concealed peripheral hem, the mesh 19 being sewn in-between the fabric plies 11 and 12 of bottom sheet 3. Fenestrations 16 and 17 are also preferably finished with peripheral concealed hems.

The fabric plies 11 and 12 of bottom sheet 3 are preferably made of liquid repellent material. An example of appropriate liquid repellant material for this purpose is that available from Standard Textile Co., Inc. of Cincinnati, Ohio under the trademark ComPel®. The mesh material 19 may be made, for example, of polyester.

The overall drape structure 1 is achieved by sewing top sheet 2 and bottom sheet 3 together. It should be noted that the combined length of the edges 9a, 9b and 9c of the triangular cut-out 9 in top sheet 2 is substantially equal to the overall length of the top edge 20 of bottom sheet 3. The end 20a is matched with the end 9d of the side edge 9a of triangular cut-out 9 and the top edge 20 of bottom sheet 3 is sewn along edge 9a, edge 9b and 9c so that the end 20b of edge 20 corresponds with and meets the end 9e of the side edge 9c of triangular cut-out 9. It will be understood that the plies 11 and 12 will be properly in-turned along edge 20 so as to provide a finished edge. The fabric of top sheet 2 will also be in-turned along edges 9a, 9b and 9c to provide finished edges.

By sewing together the top edge 20 of bottom sheet 3 and the edges 9a, 9b and 9c of top sheet 2 there is automatically formed a pair of gussets in the drape 1 to accommodate the legs of the patient when properly positioned for the procedure. The gussets are generally indicated in FIG. 1 at 21 and 22. On the left side, a portion of bottom sheet 3 is folded underneath. On the right side of FIG. 1, a part of top sheet 2 is folded underneath. The end point 9d/20a and 9e/20b are clearly shown, as are the sewn together edge segments 9a/20, 9b/20 and 9c/20.

The drape 1 is completed by the provision of a flap member, generally indicated at 23. The flap member 23 (as viewed in FIG. 1) is made up of an upper rectangular portion 23a and a lower substantially triangular portion 23b. The upper flap portion 23a has rounded upper corners 23c and 23d. The lower flap portion 23b has a rounded lowermost end 23e.

Figure 4:
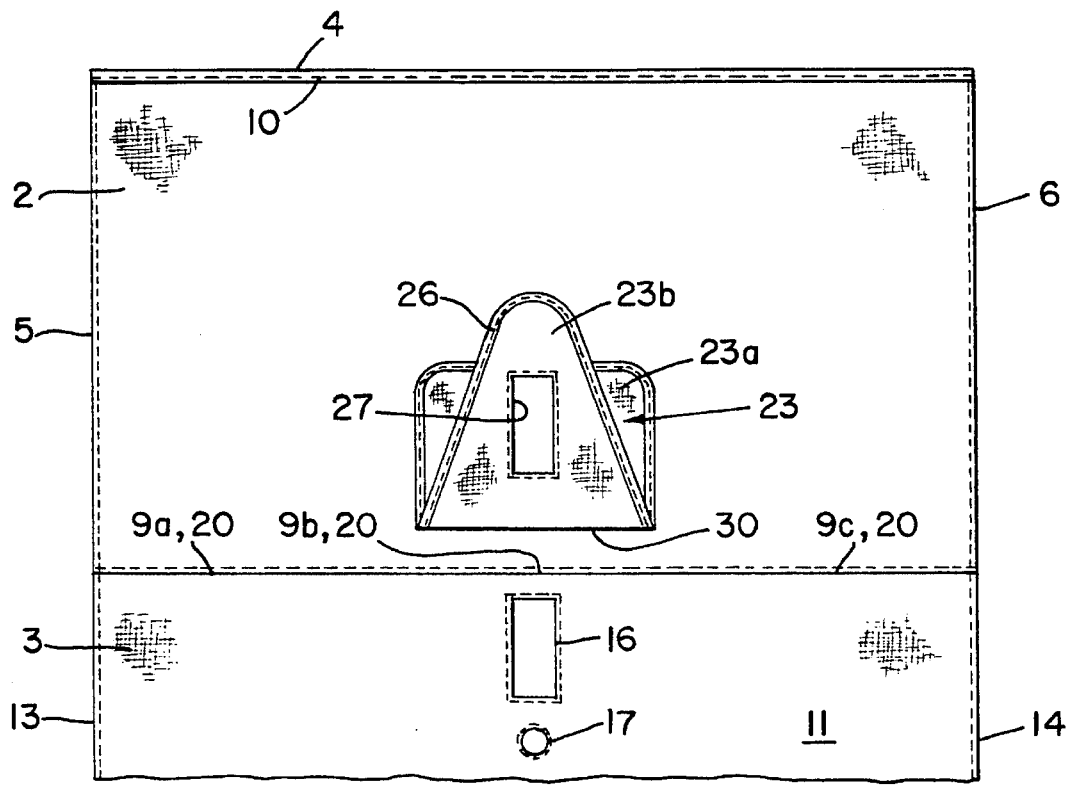
FIG. 4 is a fragmentary plan view of the drape of the present invention, illustrating the unattached portion of the flap member in its folded or retracted position.
Figure 5:
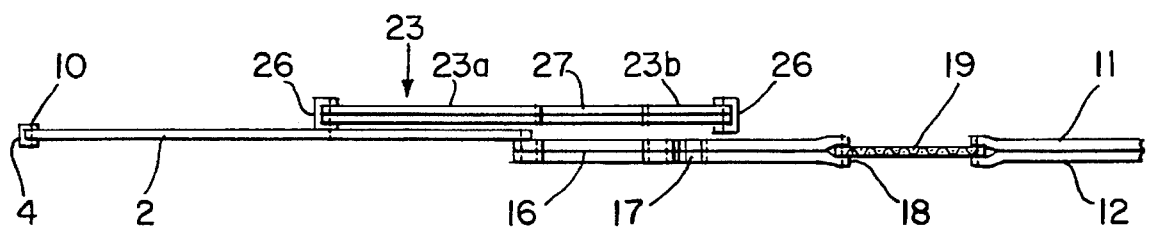
FIG. 5 is a cross-sectional view taken along section line 5–5 of FIG. 1.

The flap member 23 is comprises an upper layer 24 and a lower layer 25 (see FIGS. 4 and 5). The lower layer 25 of flap member 23 is preferably made of a liquid repellent material such as ComPel®, mentioned above. The upper layer 24 of flap member 23 is preferably made of an absorbent, textured material, such as that sold by Standard Textile Co., Inc. of Cincinnati, Ohio under the mark ZORWIK™. The fabric layers 24 and 25 are peripherally sewn together and the peripheral edges of the layers are finished with a binding tape 26 which may also be made of liquid repellent material such as the above-mentioned ComPel®.

The flap member 23 is provided with a fenestration 27, the peripheral edges of which are preferably finished with a hidden hem. The fenestration 27 is substantially identical in size and shape to the fenestration 16 of bottom sheet 3.

The upper rectangular portion 23a of flap member 23 is sewn directly to top sheet 2. To this end, the peripheral edges of the rectangular portion 23a of flap member 23 are sewn directly to top sheet 2 from a first reinforcing bartack 28 to a second reinforcing bartack 29. The reinforcing bartacks 28 and 29 define between them an imaginary fold line 30 along which the lower portion 23b of the flap member 23 folds when shifted from its normal closed position shown in FIG. 1 to its folded open position shown in FIG. 4. It will be noted that when the flap member portion 23b is in its closed position, its fenestration 27 overlies and is substantially coextensive with the first fenestration 16 of the drape bottom sheet 3. The flap member portion 23b, however, covers the fenestration 17 of bottom sheet 3. When flap member portion 23b is in its folded open position, as shown in FIG. 4, bottom sheet fenestration 16 remains open, and bottom sheet fenestration 17 is uncovered.

FIG. 5 is a diagrammatic cross-sectional view taken along section 5—5 of FIG. 1 and illustrates the various fabric plies. It will be understood that the plies in FIG. 5 are shown greatly exaggerated in thickness for purposes of clarity. For this reason, the various infolds and hems at the ply edges have been omitted.

In an exemplary embodiment of the drape of the present invention, the top sheet upper edge 4 was 60 inches long. The side edges 5 and 6 were 53 inches long. The bottom edge segments 7 and 8 of top sheet 2 were 29 inches long. Finally, the edges 9a and 9c of triangular cut-out were 22 inches long and the joining edge 9b was 16 inches long.

In the above-mentioned exemplary embodiment of drape 1, the bottom sheet had a length of 60 inches and a width of 60 inches. The first bottom sheet fenestration 16 had a width of three inches and length of seven inches. The flap fenestration 27 was similarly dimensioned. The second bottom sheet fenestration 17 was circular and had a diameter of two inches. The distance between adjacent edges of bottom sheet first fenestration 16 and second fenestration 17 was two inches. The bottom sheet opening 18 was 10 inches wide and 10 inches long and the mesh screen was of just slightly larger dimensions so that it could be sewn between the bottom sheet plies 11 and 12. The fenestrations 16 and 17 and the opening 18 were centered on bottom sheet 3 between the sides 13 and 14 thereof.

The distance from the top edge 4 of drape 1 to the top edge 26 of flap member 23 was 20 inches. The distance from the drape top edge 4 to the top edges of fenestrations 16 and 27 (with the flap in its unfolded closed position) was 35 inches. The overall width of the flap member was 15 inches, and its overall length was 28 inches. The distance from the top edge of the flap member to the imaginary fold line 30 was 11 inches.

It will be understood that the dimensions given above are exemplary only. Of importance, however, is the fact that the first fenestration 16 of bottom sheet 3 and the fenestration 27 of flap member 23 be of substantially the same dimensions and that, when the flap portion 23b is in its unfolded closed position, the fenestrations 16 and 27 are coextensive, and the flap covers the second fenestration 17 of bottom sheet 3.

In use, the cystoscopic procedure is performed through the aligned, coextensive fenestrations 16 and 27, with the flap member portion 23b being in its closed unfolded position. This causes the fenestrations to be surrounded by the outer layer of absorbent, textured material, such as the above-mentioned Zorwik™. Fluid runoff from the fenestrations 16 and 27, during the cystoscopic procedure, will pass through drape opening 18 to an appropriate fluid collecting device (not shown). The mesh 19 serves as a filter to collect any particulate matter from the fluid runoff. The upper rectangular portion 23a of flap member 23, located between its upper edge 30a and the imaginary fold line 30 may constitute a work area upon which instruments may be rested, or the like, during the cystoscopic procedure.

When a rectal examination is to be performed, following the cystoscopic procedure, the flap member portion 23b is shifted to its folded, open position, as illustrated in FIG. 4. Under these circumstances, fenestration 17 is uncovered and accessible, and is formed in and surrounded by liquid repellant fabric such as the above-mentioned ComPel®.

It will be evident that the drape of the present invention is a reusable drape and is capable of being subjected to any of the well-known sterilization processes, including autoclaving.

Figure 6:
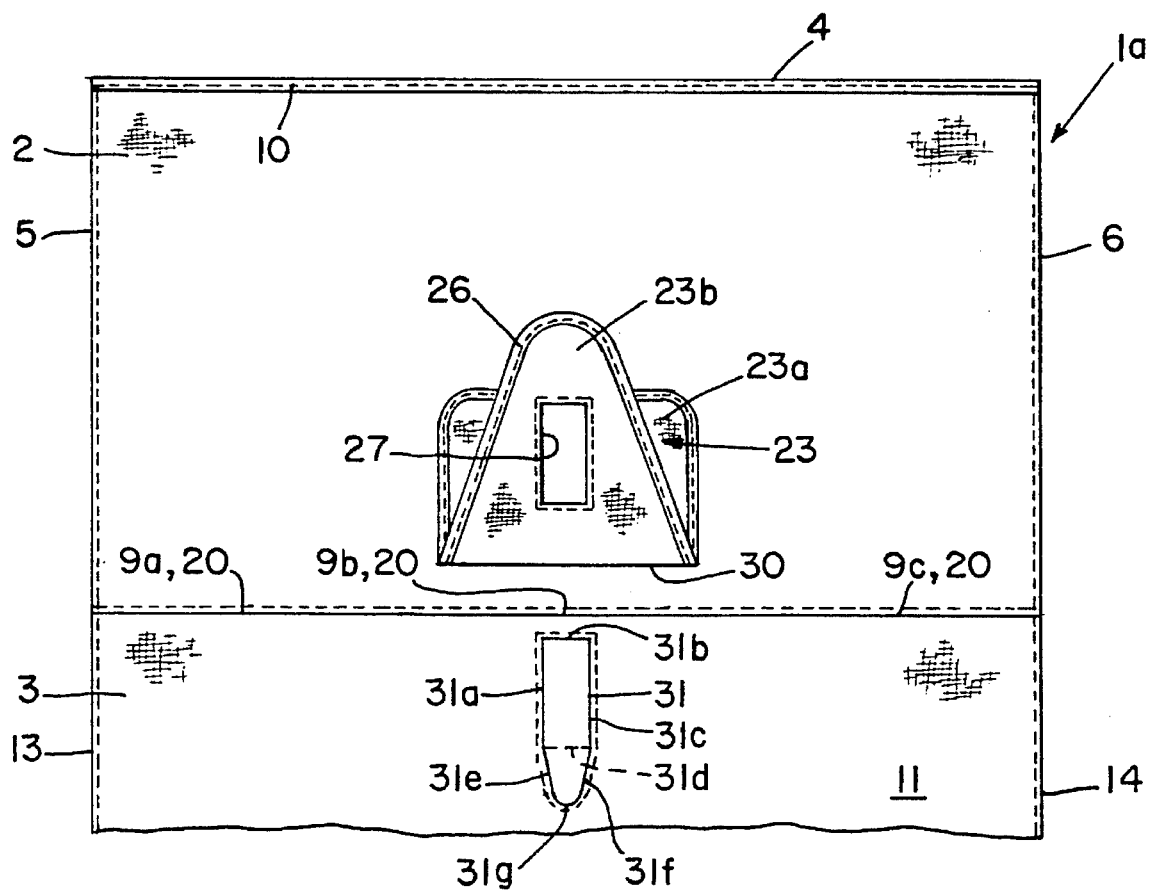
FIG. 6 is a fragmentary plan view, similar to FIG. 4, and illustrating a second embodiment of the present invention.

Reference is now made to FIG. 6. FIG. 6 is a fragmentary plan view similar to FIG. 4 and illustrating a second embodiment of the drape of the present invention. To this end, the overall drape is generally indicated at 1a. Like parts have been given the same index numerals as found in FIGS. 1–5. The only difference between the embodiment of FIG. 6 and the embodiment of FIGS. 1–5 lies in the fact that the bottom sheet fenestrations 16 and 17 of FIGS. 1 and 3 have been merged into a single fenestration 31. The rectangular portion of fenestration 31 is defined by its edge portions 31a, 31b and 31c, together with an imaginary line drawn between the lower ends of edge portions 31a and 31c and indicated in dotted lines at 31d. The rectangular portion of fenestration 31 may be substantially identical to fenestrations 16 and 27, previously described. The remainder of fenestration 31 is defined by the above noted imaginary line 31d extending between the ends of edge portions 31a and 31c together with downwardly and inwardly sloping edge portions 31e and 31f, and joining arcuate edge portion 31g. This lower, substantially triangular or U-shaped portion of fenestration 31 is basically equivalent to the fenestration 27 of embodiment 1, and serves the same purpose. With the exception of the fact that fenestration 31 is equivalent to the combination of previously described fenestrations 16 and 17, the drape 1a may otherwise be identical to the drape of embodiment 1 and is used in basically the same manner. When the flap member 23 is in its normal closed position, the flap fenestration 27 will overlay and will be co-extensive with the rectangular portion 31a, 31b, 31c and 31d of fenestration 31. The portion 31d, 31e, 31f and 31g of fenestration 31 will be covered by the flap. The fenestration 27 and the equivalent rectangular portion of fenestration 31 will still be surrounded by a fluid absorbent, textured fabric such as the above noted Zorwik™. When the flap portion 23b is in its open position, all of fenestration 31, including the lower U-shaped or substantially triangular portion 31d, 31e, 31f and 31g will be exposed and totally surrounded by water repellant fabric, such as the above noted ComPel®.

As used herein and in the claims, terms such as "top", "bottom", "upper", and "lower", are employed in conjunction with the drawings for purposes of clarity to help locate parts as viewed in the drawings. It will be appreciated that various parts of the drape will assume various different orientations during actual use of the drape.

Modifications may be made in the invention without departing from the spirit of it.

What is claimed:

1. A reusable surgical drape having top, bottom and side edges, said drape having first and second fenestration portions formed therein, a flap member having a fixed portion attached to said drape and a movable flap portion having a fenestration formed therein, said flap fenestration being of the same size and shape as said first drape fenestration portion, said flap portion of said flap member being shiftable between an unfolded covering position and a folded uncovering position, said flap portion of said flap member, when in said unfolded covering position, overlying said first and second drape fenestration portions with said second fenestration of said drape being covered thereby and said flap portion fenestration overlying said drape first fenestration portion and being coextensive therewith, said first and second drape fenestrations being exposed when said flap portion is in said folded uncovering position.

2. The reusable surgical drape claimed in claim 2 wherein said first and second fenestration portions comprise first and second adjacent parts of a single elongated fenestration.

3. The reusable surgical drape claimed in claim 1 wherein said first and second fenestrations comprise separate adjacent fenestrations.

4. The reusable surgical drape claimed in claim 1 wherein said drape comprises a top sheet and a bottom sheet, said top sheet having a top edge comprising said drape top edge, side edges, and a bottom edge interrupted at its longitudinal center by a three sided triangular opening formed in top sheet, said bottom sheet having a top edge, side edges and a bottom edge comprising said bottom edge of said surgical drape, said top edge of said bottom sheet being sewn along said three sides of said triangular opening whereby to form gussets in said drape to accommodate the patient's legs, said drape fenestration portions being formed in said bottom sheet, and said fixed portion of said flap member being attached to said top sheet adjacent said bottom sheet with said flap portion, when in said unfolded covering position overlying said drape fenestration portions in said bottom sheet.

5. The reusable surgical drape claimed in claim 4 wherein said top sheet comprises a single ply of a sterilizable low liquid repellent fabric, said bottom sheet comprises two plies of sterilizable highly liquid repellant fabric, said flap member comprises upper and lower fabric plies, said lower ply being a sterilizable highly liquid repellant material, said upper ply being a sterilizable absorbent textured fabric.

6. The reusable surgical drape claimed in claim 5 wherein said first and second fenestration portions comprise first and second adjacent parts of a single elongated fenestration.

7. The reusable surgical drape claimed in claim 6 including an opening in said drape between said drape second fenestration portion and said drape bottom edge, said opening comprising a draining opening for fluids, said drainage opening is covered with a fabric mesh.

8. The reusable surgical drape claimed in claim 5 wherein said first and second fenestrations comprise separate adjacent fenestrations.

9. The reusable surgical drape claimed in claim 8 including an opening in said drape between said drape second fenestration portion and said drape bottom edge, said opening comprising a draining opening for fluids, said drainage opening is covered with a fabric mesh.

10. The reusable surgical drape claimed in claim 1 including an opening in said drape between said drape second fenestration portion and said drape bottom edge, said opening comprising a draining opening for fluids, said drainage opening is covered with a fabric mesh.

11. The reusable surgical drape claimed in claim 1 wherein said drape comprises a drape for a cystoscopic procedure.

* * * * *